US005703026A

United States Patent [19]

Setser et al.

[11] Patent Number: 5,703,026
[45] Date of Patent: Dec. 30, 1997

[54] SKIN CLEANSING BAR SOAP COMPOSITIONS COMPRISING PARTICLES OF ABSORBENT GELLANT MATERIALS

[75] Inventors: Drew Douglas Setser, Montgomery; George Endel Deckner, Cincinnati, both of Ohio

[73] Assignee: The Procter & Gamble Company, Cincinnati, Ohio

[21] Appl. No.: 456,987

[22] Filed: Jun. 1, 1995

[51] Int. Cl.$^6$ ............................................. C11D 9/04
[52] U.S. Cl. .................... 510/152; 510/155; 510/440; 510/450; 510/476
[58] Field of Search ............................... 510/152, 155, 510/440, 450, 476, 477

[56] References Cited

U.S. PATENT DOCUMENTS

| | | | |
|---|---|---|---|
| 4,172,122 | 10/1979 | Kubik et al. | 424/59 |
| 4,508,705 | 4/1985 | Chaudhuri et al. | 424/47 |
| 4,650,670 | 3/1987 | Callingham et al. | 424/65 |
| 4,659,560 | 4/1987 | Bews et al. | 424/47 |
| 4,673,525 | 6/1987 | Small et al. | 252/132 |
| 4,708,863 | 11/1987 | Bews et al. | 424/47 |
| 4,743,440 | 5/1988 | Callingham et al. | 424/46 |
| 4,822,596 | 4/1989 | Callingham et al. | 424/46 |
| 4,828,752 | 5/1989 | Nagarajan | 510/130 |
| 4,969,925 | 11/1990 | Sisco et al. | 510/151 |
| 4,985,170 | 1/1991 | Dawson et al. | 510/476 |
| 5,246,615 | 9/1993 | Broadwell et al. | 510/476 |
| 5,409,640 | 4/1995 | Giret et al. | 510/417 |
| 5,605,681 | 2/1997 | Trandai et al. | 424/65 |

FOREIGN PATENT DOCUMENTS

WO 91/16037  10/1991  WIPO .............................. C11D 3/37

OTHER PUBLICATIONS

Appl. #89/7714, Oct. 11, 1989, South Africa.

*Primary Examiner*—Prince Willis, Jr.
*Assistant Examiner*—Cephia D. Toomer
*Attorney, Agent, or Firm*—D. F. Nesbitt; M. B. Graff; D. E. Hasse

[57] ABSTRACT

The subject invention relates to skin cleansing bar soap compositions comprising:
(a) from about 40% to about 95% surfactant component comprising fatty acid soap and/or synthetic surfactant, such that the composition comprises:
  (1) from 0% to about 95% fatty acid soap;
  (2) from 0% to about 50% synthetic surfactant;
(b) particles of absorbent gellant material, the amount of absorbent gellant material, dry weight basis, in the composition being from about 0.02% to about 5%, the absorbent gellant material having an extractable polymer content of less than about 25%;
(c) from about 5% to about 35% water;
(d) from 0% to about 25% moisturizer;
(e) from 0% to about 15% other ingredients comprising one or more of polymeric skin feel and mildness aid, perfume, solvent, colorant, antibacterial agent, and preservative.

11 Claims, No Drawings

SKIN CLEANSING BAR SOAP COMPOSITIONS COMPRISING PARTICLES OF ABSORBENT GELLANT MATERIALS

TECHNICAL FIELD

The invention relates to skin cleansing bar soap compositions comprising particles of absorbent gellant materials.

BACKGROUND OF THE INVENTION

The cleansing of skin with surface-active cleansing preparations is of interest. Many people wash and scrub their skin with various surface-active preparations several times a day. Ideal skin cleansing bars should be economical, produce creamy lather, and cleanse the skin gently, with little or no irritation and without defatting and overdrying the skin or leaving it taut after frequent routine use.

Polymeric materials have been used in bar soap compositions as thickeners, skin feel and mildness aids, and wear reducers. Examples of such bar soap compositions are disclosed, for example, in U.S. Pat. No. 4,673,525 issued to Small, Garrison, Wickler, Seaman & Papa on Jun. 16, 1987; U.S. Pat. No. 4,828,752 issued to Nagarajan on May 9, 1989; U.S. Pat. No. 4,969,925 issued to Sisco, Hill, Vinzent, Aronson & Elliott on Nov. 13, 1990; PCT Patent Application No. WO 91/16037 of Randen & Chang published Oct.31, 1991; and South African Patent Application No. 897,714 of Joshi published in 1991.

It is an object of the subject invention to provide bar soap compositions which are economical to manufacture and market.

It is also an object of the subject invention to provide bar soap compositions which are mild to the skin.

It is also an object of the subject invention to provide bar soap compositions which provide creamy lather in use.

It is also an object of the subject invention to provide bar soap compositions which provide desired skin feel during and/or after use.

It is a further object of the subject invention to provide bar soap compositions having a high level of water.

SUMMARY OF THE INVENTION

The subject invention relates to skin cleansing bar soap compositions comprising:

(a) from about 40% to about 95% surfactant component comprising fatty acid soap and/or synthetic surfactant, such that the composition comprises:

(1) from 0% to about 95% fatty acid soap;

(2) from 0% to about 50% synthetic surfactant;

(b) particles of absorbent gellant material, the amount of absorbent gellant material, dry weight basis, in the composition being from about 0.02% to about 5%, the absorbent gellant material having an extractable polymer content of less than about 25%;

(c) from about 5% to about 35% water;

(d) from 0% to about 25% moisturizer;

(e) from 0% to about 15% other ingredients comprising one or more of polymeric skin feel and mildness aid, perfume, solvent, colorant, antibacterial agent, and preservative.

DETAILED DESCRIPTION OF THE INVENTION

Materials incorporated in the bar soap compositions of the subject invention include those indicated hereinbelow. Unless otherwise specified, all percentages are on a weight basis.

Absorbent Gellant Materials

As used herein, "hydrogel" means an organic polymeric compound capable of absorbing aqueous fluids and retaining them under moderate pressures. Examples are cross-linked polymers. Cross-linking may be by covalent, ionic, vander Waals, or hydrogen bonding. Examples of polymers include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogels are those disclosed in U.S. Pat. No. 3,901,236, issued to Assarsson et al., Aug.26, 1975 and U.S. Pat. No. 4,654,039 issued to Brandt et al., Mar. 31, 1987, the disclosures of which are incorporated herein by reference. Particularly preferred polymers for use herein are polyacrylic acid grafted starch, polyacrylates, isobutylene maleic anhydride copolymers, and mixtures thereof.

Process for preparing hydrogels are disclosed in U.S. Pat. No. 4,076,663, issued Feb. 28, 1978 to Masuda et al.; U.S. Pat. No. 4,286,082, issued Aug. 25, 1981 to Tsubakimoto et al.; and further in U.S. Pat. Nos. 3,734,876, 3,661,815, 3,670,731, 3,664,343, 3,783,871, and Belgian Patent Number 785,858; the disclosures of all of which are incorporated herein by reference.

As used herein, "absorbent gellant material" or "AGM" means hydrogels having a low extractable polymer content. Extractable polymer content of a polymeric material is determined as provided hereinbelow. Preferred AGMs useful in the subject invention are hydrogels having an extractable polymer content of less than about 25%, more preferably less than about 20%, more preferably still less than about 15%, also preferably less than about 10%, also preferably from about 8% to about 12%.

Preferred AGMs include the following: cross-linked acrylate copolymer partially neutralized to sodium salt sold under the trade name Oasis® from Technical Absorbents Limited; partially neutralized sodium polyacrylates sold by Nalco, Nippon Shokubai (L series), Stockhausen (SXM® series), Chemdal (Aridall® series), Dow XZ®, Nippon Goshi®, and Sumitomo Seika (Aquakeeps® series); olefin/alkyl carboxylate copolymer inorganic salts such as isobutylene maleic anhydride copolymer sold by the Camelot Corporation under the trade names Fiberdri® fiber and Fibersorb®; starch-grafted sodium polyacrylates sold by Paragon, Sanyo, and Hoechst Celanese; starch grafted acrylate/acrylamide copolymers sold under the Water Lock® name by Grain Processing Corp; and mixtures of polyacrylate and starch grafted polyacrylates sold by Moony under the trade name Power Slims®.

In order to achieve desired water absorption by polyacrylic acid-based AGMs, such AGMs are preferably neutralized (be in salt form rather than acid form) in the subject invention compositions. In order to maximize their capacity to absorb water, these materials must be neutralized to a salt form. Such polymers are preferably neutralized to a salt previous to being incorporated in the subject invention compositions. Alternatively, sufficient base may be incorporated in the subject invention compositions to neutralize the polymers in situ in the compositions. The neutralized polyacrylic acid-based AGMs are preferably in the form of a monovalent salt, such as an alkali metal salt, preferably sodium or potassium, especially sodium, or an ammonium salt. Polyacrylic acid-based AGMs in the subject compositions are preferably at least about 50% neutralized, more preferably at least about 70% neutralized, more preferably still about 100% neutralized.

More preferred AGMs useful in the subject invention include the following: starch-grafted sodium polyacrylates, such as those sold under the Sanwet® name by Hoechst Celanese Co.; starch grafted acrylate/acrylamide copolymers, such as those sold under the Water Lock® name by Grain Processing Corp.; partially neutralized sodium polyacrylates, such as those sold by Nalco Corp., Shokubai Corp., and under the name Aridall® by the Chemdal Corp.; and isobutylene maleic anhydride copolymer, such as those sold under the Fibersorb® name by the Camelot Corp.

Especially preferred AGMs include starch-grafted sodium polyacrylates available from Hoescht Celanese Co. under the trademarks SANWET COS 905, 915, 930, 960 and 965®; and partially neutralized sodium polyacrylates available from Nalco Co. under the trademark Nalco 1181®.

The AGMs are present in the bar soap compositions of the subject invention at levels, on a dry weight basis, of from about 0.02% to about 5%, preferably from about 0.05% to about 2%, more preferably from about 0.1% to about 0.9%, most preferably from about 0.2% to about 0.5% of the bar soap.

The AGMs are incorporated in the bar soap compositions of the subject invention starting as dry particles which are mixed with other ingredients of the compositions. Because of the low extractable polymer content of the AGMs, they remain as discrete particles in the bar soap compositions, even when swelled by the absorption of water incorporated in the bar soap compositions. As discrete particles in the soap, the AGM's do not substantially dilute the effectiveness of the continuous soap phase; they do not have any substantial negative effect on the performance of the soap.

As used herein, "particles" include particles of any shape, e.g. spherical or semi-spherical, cubic, rod-like, polyhedral, etc.; but also shapes having a large greatest dimension/smallest dimension ratio, like needles, flakes and fibers, are contemplated. By "average particle size", as used herein, is meant the weight average of the largest dimension of the individual particles, when the particles are dry.

The preferred particle size of dry AGM particles incorporated in the bar soap compositions of the subject invention is preferably less than about 200 microns, more preferably from about 10 microns to about 100 microns, more preferably still from about 20 microns to about 80 microns, most preferably from about 30 microns to about 50 microns.

Many of the AGM products commercially available have average particle sizes larger than those preferred for the subject invention. For such materials, it is preferred that the particle size of the AGMs be reduced prior to incorporating into the subject invention compositions, for example by grinding, chopping, etc. or during making of the subject invention compositions, e.g., by homogenizing, etc.

Test Methods for Extractable Polymer Content

Depending upon the type of AGM involved, two different methods are used to determine extractable polymer content. For carboxylic acid-based AGMs, a potentiometric procedure is used to determine extractables. For non-carboxylic acid-based AGMs, a gravimetric procedure is employed. It should be noted that both of these procedures may provide results that include, in the total amount of extractable material, those extractable components in the AGM which are not polymeric. Therefore, if a given polymer sample is known or believed to contain significant amounts of non-polymeric extractable material, such non-polymeric extractable material should be removed from the analyte in conventional fashion before running the extractable polymer content determination hereinafter described.

1. Carboxylic Acid-Based AGMs

Extractable polymer content of carboxylic acid-based AGMs is determine by admixing the AGM with a 0.9% saline solution for a period of time sufficient to substantially approach equilibrium with respect to extraction of polymer material from the gel which is formed. The water mixture is allowed to settle and a portion thereof is filtered. An aliquot of this filtrate is then taken, and the free acid groups on the polymer material dissolved in this filtrate are titrated to pH 10 with base. All of the carboxylate groups are then titrated to pH 2.7 with acid. These titration data are then used to calculate the amount of extractable polymer in the AGM sample.

(a) Preparation of the Extractable Polymer-Containing Filtrate Samples 1. 0.40 to 0.41 g of AGM is accurately (to ±0.1 mg) weighed into a 150 ml disposable beaker. If glass beakers are used, they must be acid washed prior to use. Glassware should be washed three times with dilute HCl (conc. HCl diluted 1:4 with distilled water), then three times with distilled water. This procedure removes traces of detergents and other contaminants which would otherwise interfere with the titration.

2. 75 ml of a 0.9% NaCl aqueous solution is added.

3. Samples are slowly stirred for a period of time sufficient to reach equilibrium. Equilibrium is generally reached within 16 hours. If extractable polymer content is to be measured as a function of time, then 1, 6, and 16 hour periods are sufficient to define the extractables versus time curve.

4. Samples are allowed to settle for 15 minutes. The sample may be centrifuged to aid separation of the solution from the solid gel.

5. Using a 3 ml disposable syringe and 0.22 micron filters, enough solution is filtered so that a 20 ml aliquot can be taken.

(b) Titration Conditions

1. If the titrations are to be performed manually, great care must be taken to assure that equilibrium is reached after each addition of titrant.

2. A 20 ml aliquot of the filtrate is transferred to a 50 ml disposable beaker. If glass beakers are being used, they must be acid washed prior to use as noted hereinabove.

3. The aliquot is titrated to pH 10 with 0.1N NaOH.

4. The aliquot is then back titrated to pH 2.7 with 0.1N HCl.

5. Steps 3 and 4 are performed on 20 ml of the 0.9% NaCl solution to obtain titration blanks for both steps of the titration.

(c) Calculations

1. The amount of polymerized acid moieties (e.g., acrylic acid) (in millimoles) in the supernatant aliquot ($M_a$) is given by:

$$M_a = (V_a - V_{ab}) \times N_a \text{ millimoles (mm)}$$

where:

$V_a$=the volume (in ml) of acid required to titrate the aliquot to pH 10;

$V_{ab}$=the volume (in ml) of acid required to titrate 20 ml of saline solution to pH 10;

$N_a$=the normality (in meq/ml) of the acid (nominally 0.10 meq/ml).

2. The total amount of polymerized acid moieties (e.g. acrylic acid) plus polymerized neutralized acid moieties (e.g., sodium acrylate) (in mm) in the supernatant aliquot ($M_t$) is given by:

$$M_t=(V_b-V_{bb}) \times N_b \text{ millimoles}$$

where:

$V_b$=the volume (in ml) of base required to titrate the aliquot from pH 10 down to pH 2.7;

$V_{bb}$=the volume (in ml) of base required to titrate 20 ml of saline solution from pH 10 down to pH 2.7;

$N_b$=the normality (in meq/ml) of the base (nominally 0.10 meq/ml).

3. The amount of polymerized neutralized acid moieties (e.g., sodium acrylate) (in mm) in the original supernatant aliquot ($M_b$) is given by:

$$M_b = M_t - M_a.$$

4. The total amounts of polymerized acid moieties ($W_a$) and polymerized neutralized acid moieties ($W_b$) (e.g., acrylic acid plus sodium acrylate) extracted (in mg) are given by:

$$W_a = M_a \times E_a \times D \text{ and } W_b = M_b \times E_b \times D$$

where:

$E_a$=The equivalent weight of acid moiety in polyacid moiety (e.g., acrylic acid in polyacrylic acid=72 meq/mg);

$E_b$=The equivalent weight of neutralized acid moiety in neutralized polyacid moiety (e.g., sodium acrylate in sodium polyacrylate=94 meq/mg);

D=The dilution factor (75 ml/20 ml=3.75).

5. The percent extractable polymer in the AGM samples (e) is given by:

$$e=((W_a+W_b) \times 100)/W$$

where:

W=the sample weight in mg.

2. Non-Carboxylic Acid-Containing AGMs

Extractable polymer content of non-carboxylic acid-based AGMs is determined by a gravimetric procedure wherein AGM samples are swollen overnight in distilled water, and the polymer content in the filtrate is gravimetrically determined. The particular procedure of the gravimetric extractables determination are set forth as follows:

Into a 500 ml Erlenmeyer flask is weighed accurately (to ±0.1 mg) about 0.25 grams of dry AGM ($W_p$). 250 ml of distilled water is added, and the mixture is stirred slowly for 1 hour. After this hour has passed, stirring is stopped, and the swollen gel is allowed to settle overnight. In the morning enough of the supernatant is filtered using a 3 ml disposable syringe and 0.22 micron filter to obtain at least 40 ml of filtrate. Exactly 40 ml of filtrate is placed into a clean 100 ml round-bottom flask, and the solution is concentrated on a rotary evaporator (water aspirator vacuum, bath temperature 55° C.). The remaining 2–3 ml of solution is transferred quantitatively to a tared weighing vial with the aid of additional distilled water. The solution in the weighing vial is reduced to dryness in an oven at 120° C. The vial is cooled, reweighed, and the weight of residue ($W_r$) is determined using the tare weight of the vial. The percent extractable polymer (e) is calculated from the weight of dry polymer ($W_p$) and weight of residue ($W_r$) by the following equation:

$$e=((W_r \times 250) \times 100)/(W_p \times 40).$$

Surfactants

The bar soap compositions of the subject invention comprises a surfactant component comprising fatty acid soap and/or synthetic surfactant. The weight percent of surfactant in the subject invention compositions is from about 40% to about 95%, preferably from about 50% to about 90%, more preferably from about 60% to about 85%, more preferably still from about 70% to about 80%.

Fatty acid soaps are alkali metal soaps of fatty acids having alkyl chain lengths of about $C_8$–$C_{22}$, preferably about $C_{12}$–$C_{18}$, and especially those of about $C_{12}$–$C_{14}$ chain lengths which are important in producing lather rapidly and of good, highly acceptable quality. Preferred soaps include those made from fatty acids derived from natural sources such as plant or animal-derived glycerides, e.g., coconut oil, tallow, palm kernel oil, babassu oil, soybean oil, castor oil, whale oil, fish oil, grease, lard, palm stearin oil and mixtures thereof. The fatty acids can be synthetically prepared, e.g., by oxidation of petroleum stocks or by the Fischer-Tropsch process.

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and/or tallow, i.e., sodium and potassium tallow and coconut soaps.

The term "tallow", as used herein, means glycerides or fatty derivatives therefrom with fatty acid mixtures which typically have an approximate carbon chain length distribution of about 2–4% $C_{14}$, 25–35% $C_{16}$, 20–25% $C_{18}$, 1–3% palmitoleic, 35–45% oleic and 2–4% linoleic (the first three fatty acids listed are saturated). Other sources with similar fatty acid distributions, such as the fatty acids derived from palm stearin oil and from various animal tallows and lard, are also included within the term tallow. The tallow can also be hardened (i.e., hydrogenated) to convert part or all of the unsaturated fatty acid moieties to saturated fatty acid moieties.

The term "coconut oil" as used herein, means glycerides or fatty derivatives therefrom with fatty acid mixtures which typically have an approximate carbon chain length distribution of about 5–10% $C_8$, 5–10% $C_{10}$, 45–55% $C_{12}$, 15–20% $C_{14}$, 5–10% $C_{16}$, 1–3% $C_{18}$, 5–10% oleic, and 1–3% linoleic (the first six fatty acids listed being saturated). Other sources having similar fatty acid distributions, such as palm kernel oil and babassu oil, are included with the term coconut oil.

The fatty acid soaps are present in the bar soap compositions of the subject invention at a level of from 0% to about 95%, preferably from about 30% to about 90%, more preferably from about 40% to about 85%, more preferably still from about 50% to about 80%, most preferably from about 60% to about 75%. A preferred soap consists of tallow soap and coconut soap, and preferably has a ratio of tallow soap:coconut soap of from about 0.1:1 to about 9:1, more preferably from about 1:1 to about 4:1.

The soap bars of the subject invention can contain synthetic surfactants. If synthetic surfactant is included, mild ones are preferred. A mild synthetic surfactant is defined herein as one which does relatively little damage to the barrier function of the stratum corneum. Standard tests are well known for determining relative mildness of surfactants.

Synthetic surfactants are present in the subject compositions at a level of from 0% to about 50%, preferably from 0% to about 20%, more preferably still from about 0% to about 15%.

Some preferred mild synthetic surfactants useful in the subject invention compositions include alkyl glyceryl ether sulfonates (AGS), anionic acyl sarcosinates, methyl acyl taurates, N-acyl glutamates, alkyl glucosides, acyl isethionates, alkyl sulfosuccinates, alkyl phosphate esters, ethoxylated alkyl phosphate esters, ethoxylated alkyl alcohols, alkyl sulfates, alkyl ether sulfates, methyl glucose esters, protein condensates, mixtures of alkyl ether sulfates and alkyl amine oxides, betaines, sultaines, and mixtures thereof. Included in the synthetic surfactants are the alkyl ether sulfates with from about 1 to about 12 ethoxy groups, especially ammonium and sodium lauryl ether sulfates. Alkyl chain lengths for these surfactants are about $C_8-C_{22}$, preferably about $C_{10}-C_{18}$. The alkyl portion of such synthetic surfactants are often derived from natural sources of fatty acids which are the same as for the fatty acid soaps.

Water

The soap bars of the subject invention comprise from about 5% to about 35% water; preferably from about 10% to about 30% water; also preferably from about 16% to about 25% water, also preferably from about 20% to about 30%, also preferably from about 25% to about 35%.

Moisturizers/Emollients

Moisturizers may be included in the bar soap compositions of the subject invention to provide skin conditioning benefits and to improve mildness of the products. The selection of the levels and types of moisturizers to be incorporated into the products is made without adversely affecting the stability of the product or its in-use characteristics, thereby delivering good moisturization and lather.

The term "moisturizer" is often used within the cosmetic industry without very exact definition. The term is sometimes used as synonymous with emollient, and is then meant to describe a material which imparts a smooth and soft feeling to the skin surface.

There are two ways of reducing water loss from the stratum corneum. One is to deposit on the surface of the skin an occlusive layer which reduces the rate of evaporation. The second method is to add nonocclusive hygroscopic substances to the stratum corneum which will retain water, and make this water available to the stratum corneum to alter its physical properties and produce a cosmetically desirable effect. Nonocclusive moisturizers also function by improving the lubricity of the skin.

Both occlusive and nonocclusive moisturizers are suitable for use in the subject invention compositions. Some examples of moisturizers are long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanoline alcohol (e.g., Solulan-75® available from the Amerchol Co.).

Preferred moisturizers are coconut and tallow fatty acids. Other preferred moisturizers are nonocclusive liquid water-soluble polyols (e.g., glycerin, propylene glycol, butylene glycol, hexylene glycol, polypropylene glycol and polyethylene glycol). An especially preferred moisturizer is a mixture of coconut fatty acid and glycerin having a coconut fatty acid:glycerin ratio of from about 2:1 to about 0.5:1.

Other preferred nonocclusive moisturizers are compounds found to be naturally occurring in the stratum corneum of the skin, such as sodium pyrrolidone carboxylic acid, lactic acid, urea, L-proline, guanidine and pyrrolidone. Examples of other nonocclusive moisturizers include hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), hydrolyzed protein and other collagen-derived proteins, aloe vera gel and acetamide MEA (N-acetyl ethanolamine).

Other examples of both occlusive and nonocclusive types of moisturizers are disclosed in "Emollients—A Critical Evaluation," by J. Mausner, Cosmetics & Toiletries, May 1981, incorporated herein by reference.

Some occlusive moisturizers include petrolatum, mineral oil, beeswax, silicones, lanolin and oil-soluble lanolin derivatives, saturated and unsaturated fatty alcohols such as behenyl alcohol, squalene and squalane, and various animal and vegetable oils such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazelnut oil, olive oil, grape seed oil and sunflower seed oil.

Moisturizers are present in the compositions of the subject at levels of from 0% to about 25%, preferably from about 2% to about 20%. A more preferred level of moisturizers is from about 4% to about 15%; more preferred still is from about 8% to about 12%. The surfactant component to moisturizer ratio is preferably from about 4:1 to about 39:1, more preferably from about 9:1 to about 20:1.

Polymeric Skin Feel and Mildness Aids

Polymeric skin feel and mildness aids are optional components of the subject invention compositions. They include cationic, anionic, amphoteric, and the nonionic polymers used in the cosmetic field. Reduced skin irritation benefits as measured by patch testing of cationic and nonionic types of polymers are set out in "Polymer JR for Skin Care" Bulletin, by Union Carbide, 1977. The cationics are preferred over the others because they provide better skin feel benefits. Examples of the cationic polymers and the nonionic polymers useful in the subject invention compositions are set out below.

The amount of polymeric skin feel and mildness aids found useful in the compositions of the subject invention is from about 0.01% to about 5%, preferably from about 0.1% to about 4%, more preferably from about 1% to about 3%.

Polymer JR-400®, made by Union Carbide Corporation, is a preferred polymer. Others include nonionic guar gums, e.g., Merquats 100 and 550® made by Calgon, JAGUAR C-14-S® made by Rhone Poulenc, Mirapol A15® made by Rhone Poulenc, and Galactasol 811® made by Aqualon; nonionic polysaccharides, e.g., nonionic hydroxypropyl guar gums such as JAGUAR HP-60® made by Rhone Poulenc; cellulosic nonionic polymers, e.g., hydroxyethylcellulose and carboxymethylcellulose; copolymers of dimethylaminoethylmethacrylate and acrylamide; and copolymers of dimethyldiallylammonium chloride and acrylamide in which the ratio of the cationic to neutral monomer units has been selected to give a copolymer having a cationic charge.

Antibacterial Agent

An antibacterial agent, if included in the subject development compositions, is preferably included in an amount which provides effective killing of bacteria on skin when the bar soap is in use. Typical amounts are from about 0.01% to about 4%, more preferably from about 0.1% to about 2%, more preferably still from about 0.5% to about 1%. The level is selected to provide the desired level of antibacterial activity and can be modified as desired. The preferred antibacterial agent is 2-hydroxy-4,2',4'-trichlorodiphenylether (Triclosan). Other halogenated antibacterial agents which can be used are set out below. Many useful antibacterial agents are known, and are disclosed in numerous references, for example, U.S. Pat. Nos. 3,835,057 and 4,714,563, both incorporated herein by reference.

Suitable antibacterial agents include, but are not limited to the following:

2-hydroxy-4,2',4'-trichlorodiphenylether (Triclosan);
2,6-dimethyl-4-hydroxychlorobenzene (PCMX);
3,4,4'-trichlorocarbanilide (TCC);
3-trifluoromethyl-4,4'-dichlorocarbanilide (TFC);
2,2'-dihydroxy-3,3',5,5',6,6'-hexachlorodiphenylmethane;
2,2'-dihydroxy-3,3',5,5'-tetrachlorodiphenylmethane;
2,2'-dihydroxy-3,3'-dibromo-5,5'-dichlorodiphenylmethane;
2-hydroxy-4,4'-dichlorodiphenylether;
2-hydroxy-3,5',4-tribromodiphenylether; and
1-hydroxyl-4-methyl-6-(2,4,4-trimethylpentyl)-2(1 H)-pyridinone (Octopirox).

Optional Ingredients

Other optional components can be included in the compositions of the subject invention. Such other components make up, in total, from 0% to about 15% of the subject invention compositions, preferably from about 1% to about 10%.

Perfumes may be used in formulating the subject bar soap compositions, generally at a level of from about 0.1% to about 1.5% of the composition. Sodium chloride, from 0% to about 2%, is often added to make the bar harder and/or easier to process. Fillers such as talc and clays may be added from 0% to about 3%. Titanium dioxide, from 0% to about 0.5%, is often added as an opacifier. Colorants, from 0% to about 0.5%, may be used. Solvents, e.g. ethanol, from 0% to about 10% may be used to reduce the opacity of the soap. Preservatives, e.g., EDTA, generally at a level of less than about 1% of the composition, may be incorporated to prevent microbiological growth.

Process

The subject invention also includes processes for incorporating the absorbent gellant materials, as defined hereinabove, in bar soap compositions.

A non-limiting general process which exemplifies the making of bar soap compositions comprises the following steps:

1. Crutching Step

A mixture containing water, fatty acid soap, synthetic surfactant, mositurizer, and NaCl are heated to ca. 150°–200° F. (65°–94° C.).

2. Vacuum Drying and Extrusion Step

The crutcher mix is vacuum dried at ca. 50 mm Hg absolute pressure to reduce the moisture content of the mix to ca. 10%. The dried crutcher mix is extruded to form the mix into noodles.

3. Amagamating Step

The noodles from Step 2 are weighed and placed in a batch amalgamator. To the noodles in the amalgamator are added: titanium dioxide, perfume, colorant solution, preservatives, water and AGM. The water and AGM may be premixed prior to addition to the amalgamator to aid in dispersing and handling the AGM. The combined ingredients are mixed thoroughly.

4. Milling Step

Three-roll soap mills are set up with all rolls at 85°–150° F. (29°–41° C.). The mixture from the amalgamator is passed through the mills to obtain a homogeneous mix. This is an intimate mixing step.

5. Plodding and Stamping Steps

A conventional plodder is set up with the barrel temperature at about 90° F.(32° C.) and the nose temperature at about 110° F.(43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then preferably stamped on a conventional soap stamping apparatus to yield the finished soap bar.

EXAMPLES

The following are non-limiting bar soap compositions of the subject invention.

| Component | Weight Percent |
|---|---|
| Example 1 | |
| 50% Sodium Tallowate/50% Sodium Cocoate Mix | 71.05 |
| Coconut Fatty Acid | 4.80 |
| Steareth-80 nonionic surfactant | 3.30 |
| Glycerine | 3.00 |
| Sodium Chloride | 1.10 |
| Titanium Dioxide | 0.25 |
| Jaguar C-15 ® Cationic guar | 0.10 |
| Starch-grafted sodium polyacrylates (Sanwet COS 915 ®) | 0.30 |
| Perfume | 1.10 |
| Water | 15.00 |
| Example 2 | |
| 80% Sodium Tallowate/20% Sodium Cocoate Mixture | 76.4 |
| Water | 19.3 |
| Glycerin | 1.6 |
| Perfume | 1.1 |
| Sodium Chloride | 0.4 |
| Titanium Dioxide | 0.4 |
| Partially neutralized sodium polyacrylates (Nalco 1181 ®) | 0.3 |
| Colorants and Preservatives | 0.5 |
| Example 3 | |
| 80% Sodium Tallowate/20% Sodium Cocoate Mix | 76.4 |
| Water | 19.3 |
| Glycerin | 1.6 |
| Perfume | 1.1 |
| Sodium Chloride | 0.4 |
| Titanium Dioxide | 0.4 |
| Isobutylene maleic anhydride copolymer (Fibersorb SA 7200 H ®) | 0.5 |
| Colorants and Preservatives | 0.5 |
| Example 4 | |
| 55% Sodium and Magnesium Tallowate/45% Sodium and Magnesium Cocoate Mix | 58.2 |
| Potassium Lauryl Sulfate | 10.5 |
| Sodium Laureth-3 Sulfate | 5.5 |

-continued

| Component | Weight Percent |
|---|---|
| Sodium Sulfate | 5 |
| Water | 14 |
| Glycerin | 2 |
| Perfume | 1.0 |
| Sodium Chloride | 2.5 |
| Titanium Dioxide | 0.5 |
| Partially neutralized sodium polyacrylates (Nalco 1181 ®) | 0.3 |
| Colorants and Preservatives | 0.5 |

Example 5

| Component | Weight Percent |
|---|---|
| Sodium Tallowate/Sodium Laurate Mix | 44 |
| Water | 27 |
| Ethanol | 8.3 |
| Propylene Glycol | 9.0 |
| Dipropylene Glycol | 5.0 |
| Sucrose | 3.0 |
| Perfume | 2.0 |
| Sodium Lauryl Ether Sulfate | 1.0 |
| Starch-grafted sodium polyacrylates (Sanwet COS 915 ®) | 0.2 |
| Colorants and Preservatives | 0.5 |

Example 6

| Component | Weight Percent |
|---|---|
| Sodium Tallowate/Sodium Laurate Mix | 44 |
| Water | 27 |
| Ethanol | 8.3 |
| Propylene Glycol | 9.0 |
| Dipropylene Glycol | 5.0 |
| Sucrose | 3.0 |
| Perfume | 2.0 |
| Sodium Lauryl Ether Sulfate | 1.0 |
| Partially neutralized sodium polyacrylates (Nalco 1181 ®) | 0.2 |
| Colorants and Preservatives | 0.5 |

Example 7

| Component | Weight Percent |
|---|---|
| 75% Sodium and Magnesium Tallowate/25% Sodium and Magnesium Cocoate Mix | 63.2 |
| Sodium Cocoglyceryl Ether Sulfonate | 16.5 |
| Water | 13.0 |
| Glycerin | 2.0 |
| Perfume | 1.0 |
| Sodium Chloride | 3.0 |
| Titanium Dioxide | 0.5 |
| Starch-grafted sodium polyacrylates (Sanwet COS 915 ®) | 0.3 |
| Colorants and Preservatives | 0.6 |

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of this invention.

What is claimed is:

1. A bar soap composition comprising:
   (a) from about 40% to about 95% surfactant component comprising fatty acid soap and/or synthetic surfactant, such that the composition comprises:
      (1) from 0% to about 95% fatty acid soap;
      (2) from 0% to about 50% synthetic surfactant;
   (b) particles of absorbent gellant material, the amount of absorbent gellant material, dry weight basis, in the composition being from about 0.02% to about 5%, the absorbent gellant material having an extractable polymer content of less than about 25%, the absorbent gellant material being selected from the group consisting of starch-grafted sodium polyacrylates, starch-grafted acrylate/acrylamide copolymers, mixtures of polyacrylate and starch-grafted polyacrylate, isobutylene maleic anhydride copolymer, and mixtures thereof;
   (c) from about 5% to about 35% water;
   (d) from 0% to about 25% moisturizer;
   (e) from 0% to about 15% other ingredients comprising one or more of polymeric skin feel and mildness aid, perfume, solvent, colorant, antibacterial agent, and preservative.

2. The composition of claim 1 wherein the composition comprises from about 0.1% to about 0.9%, dry weight basis, absorbent gellant material having an extractable polymer content of less than about 15%.

3. The composition of claim 1 wherein the composition comprises from about 0.1% to about 0.5%, dry weight basis, absorbent gellant material.

4. The composition of claim 1 wherein the composition comprises from about 16% to about 35% water.

5. The composition of claim 2 wherein the composition comprises from about 20% to about 30% water.

6. The composition of claim 1 wherein the absorbent gel material has an average particle size (dry basis) of from about 10 microns to about 100 microns.

7. The composition of claim 2 wherein the absorbent gel material has an average particle size (dry basis) of from about 10 microns to about 100 microns.

8. The composition of claim 7 wherein the composition comprises from about 16% to about 30% water.

9. The composition of claim 2 wherein the composition comprises from about 30% to about 80% fatty acid soap.

10. The composition of claim 10 wherein the composition comprises from about 40% to about 80% fatty acid soap, and from 0% to about 20% synthetic surfactant.

11. The composition of claim 1 or 7 wherein the composition comprises from about 0.1% to about 2% antibacterial agent.

\* \* \* \* \*